United States Patent [19]

Wertz et al.

[11] Patent Number: 5,167,157
[45] Date of Patent: Dec. 1, 1992

[54] NONDESTRUCTIVE INSPECTION SYSTEM FOR LAMINATED PRODUCTS

[75] Inventors: Ronald D. Wertz, Boulder; Stephen M. Horacek, Louisville; H. Kent Minet, Littleton; Robert Cormack, Boulder, all of Colo.

[73] Assignee: Ball Corporation, Muncie, Ind.

[21] Appl. No.: 675,481

[22] Filed: Mar. 26, 1991

[51] Int. Cl.⁵ ............................................. G01N 29/24
[52] U.S. Cl. ......................................... 73/627; 73/634
[58] Field of Search ................. 73/618, 619, 620, 621, 73/625, 627, 628, 624, 634, 644, 588, 597

[56] References Cited

U.S. PATENT DOCUMENTS

| | | | |
|---|---|---|---|
| 2,989,864 | 6/1961 | Bamford | 73/620 |
| 3,505,859 | 4/1970 | Byers | 73/600 |
| 3,575,043 | 4/1971 | Allen et al. | 73/619 |
| 3,857,052 | 12/1974 | Beller | 367/13 |
| 4,035,839 | 7/1977 | Eggleton et al. | 73/644 |
| 4,083,232 | 4/1978 | Heyser et al. | 73/618 |
| 4,131,026 | 12/1978 | Ries et al. | 73/625 |
| 4,350,045 | 9/1982 | Chow et al. | 73/607 |
| 4,366,713 | 1/1983 | Gilmore et al. | 73/618 |
| 4,587,849 | 5/1986 | Gross | 73/644 |
| 4,741,212 | 5/1988 | Rehwald | 73/600 |
| 4,768,155 | 8/1988 | Takishita et al. | 364/507 |
| 4,881,177 | 11/1989 | McClean et al. | 73/619 |
| 4,893,510 | 1/1990 | Ichikawa et al. | 73/620 |
| 5,048,341 | 9/1991 | Lundell et al. | 73/620 |

Primary Examiner—Hezron E. Williams
Assistant Examiner—Rose M. Finley
Attorney, Agent, or Firm—Gilbert E. Alberding

[57] ABSTRACT

An apparatus and method for inspecting multilayer articles. An article to be inspected is clamped in a liquid filled tank between a pair of focused transducers. An ultrasonic pulse is introduced to a cross section of the article from each transducer sequentially. Reflections from the surfaces and interfaces within the article are received by each transducer and transmitted to a computer for analysis. The thicknesses of the innermost layers of the article are determined by calculating the mean of the measurements from each transducer for each inner layer.

18 Claims, 8 Drawing Sheets

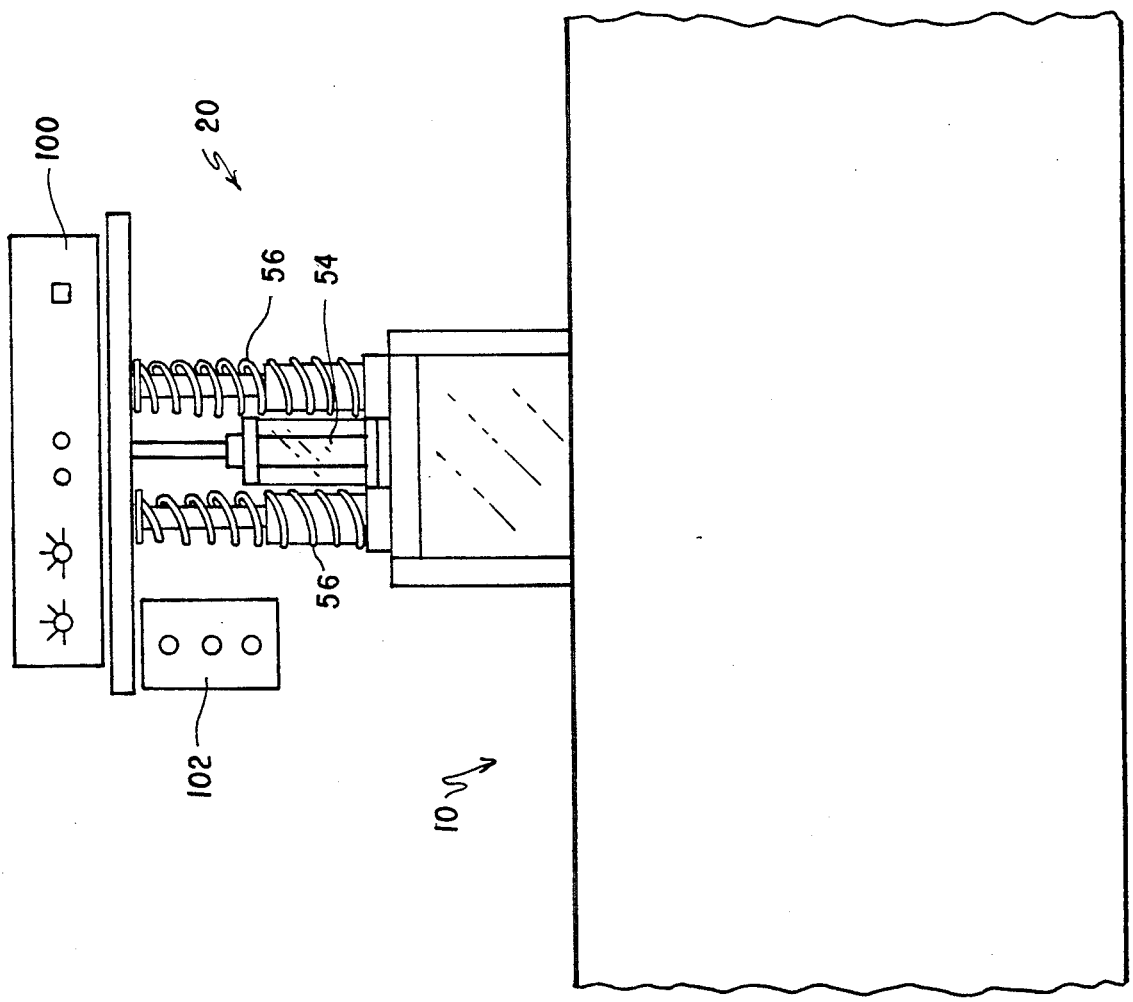

NONDESTRUCTIVE INSPECTION SYSTEM FOR LAMINATED PRODUCTS

BACKGROUND OF THE INVENTION

1. Field of the Invention

The present invention is directed to a nondestructive inspection system for multilayer articles. More particularly, the present invention is directed to an ultrasonic inspection device for laminated plastic articles.

2. Description of the Related Art

Many products in use today are composed of a plurality of individual layers. This is especially true for plastics, which are often coextruded in plastic sheets having a plurality of plastic layers. In such sheets, the layers may be formed from different materials and have different thicknesses. An appropriate combination of layers yields a product having the desired properties. For example, plastic sheets which are used to form food containers are typically multilayer in nature. These sheets can have many layers, with five or more not being uncommon. In plastic sheets used for food containers, one of the interior layers preferably functions as an oxygen barrier layer. The presence and quality of this layer have a direct bearing on the shelf life of the food product. This layer is also the most expensive to produce. One layer, for example the top layer of a sheet, has characteristics which enable it to withstand handling, while another layer, for example the bottom layer of the sheet, is designed for contacting the food product without degrading it. Intermediate layers can include tie layers for tying the top and bottom layers to the oxygen barrier layer. Regrind layers, which are made from scrap material and are therefore less expensive to produce, may also be included to function as filler layers. Such sheets can have a total thickness of, for example, from 5 to 120 mils, with the thickness of individual layers, such as the oxygen barrier layer, being as little as one mil or less.

Given the thinness and importance of such layers, it is necessary in the manufacturing process to diligently monitor layer parameters. Accordingly, quality control and sheet inspection are very serious concerns. However, no system proposed to date has proven sufficiently reliable to replace inspection by hand. Inspection by hand is labor intensive, slow, and quite costly. Typically, a sample is mechanically shaved from an edge of a coupon cut from a sheet to provide a cross-section of the sheet. The sample layer thicknesses are then optically measured under a microscope.

As can be appreciated, this inspection technique has a number of drawbacks. First of all, each article to be tested is physically invaded. While this might not matter for some laminated products, such damage to other laminated articles can render the product partially or entirely unusable. Further, in order to provide appropriate quality control, large numbers of samples must be taken. Since each sample typically takes approximately fifteen minutes to inspect, it can take one or more hours to inspect a sheet. This results in valuable production time being lost if production is held up until the quality results are verified, and the physical invasion of the article is increased. Alternatively, if production is continued while the sample is being inspected, the manufacturer runs the risk that a defective product is being produced if the test results indicate that the sample is unacceptable. Additionally, the quality of the inspection by hand itself is suspect, since the process is a multistep, labor intensive process which depends upon human accuracy in each step. Similarly, due to the time it takes to obtain results, the number of samples that can be taken is limited, thereby endangering quality control, as quality problems away from these limited areas or sampling points will not be identified using this technique.

Nondestructive inspection techniques are now used to inspect a wide variety of articles. Many of these techniques involve the transmission of ultrasonic energy into an article to be inspected. Typically, ultrasonic energy is generated by a pulser/receiver which produces an electrical pulse that excites a piezoelectric or magnetostrictive transducer, causing the transducer to emit an ultrasonic pulse. In a "pulse-echo" technique, this ultrasonic pulse travels into the article under inspection until it is reflected from an interface or internal flaw. The reflected pulse is received and converted by the transmitting transducer into an electrical signal for analysis. Another technique involves the "through transmission" of ultrasonic energy through an article to be inspected. In this technique, a signal is transmitted by a transmitting transducer, goes through the article under inspection and is received by a receiving transducer. The pulse received by the receiving transducer is converted into an electrical signal for analysis.

Such systems are able to detect, locate and record defects in the product, or the presence or absence of certain components. For example, U.S. Pat. No. 3,575,043 to Allen et al. relates to an ultrasonic inspection system for detecting defects in multicomponent assemblies. The system is capable of detecting bonding voids in the nature of approximately 1/16 inches in diameter and larger. A pair of transducers are mounted on opposite sides of a nonuniform article to be tested. As the ultrasonic transducers are moved along the surface of the non-uniform article, such as a helicopter blade, ultrasonic pulses are transmitted and received, and a C scan image is formed on recording paper. Flaws are indicated by lack of recording on the recording paper by a stylus.

U.S. Pat. No. 3,505,859 to Byers employs transmitting and receiving transducers to send ultrasonic energy through a metal object immersed in a liquid. The metal object is moved relative to the transducers during testing. If a defect is found, the article is rejected.

U.S. Pat. No. 4,587,849, which issued to Gross, employs a single transducer mounted on a production line for detecting the presence and depth of interfaces in a coextruded plastic sheet. A chamber mounted between the face of the transducer and the sheet holds an interfacing fluid through which ultrasonic pulses pass to and from the sheet.

However, nondestructive inspection systems have failed to replace the hand testing technique in measuring layer thicknesses in multilayer articles and/or in articles including extremely thin layers. It is believed that nondestructive inspection systems have proven ineffective when attempts have been made to employ them for these purposes. Accordingly, a need has arisen for a nondestructive inspection system which is capable of detecting the thicknesses of a product having a plurality of layers and/or very thin layers.

SUMMARY OF THE INVENTION

One object of the invention is to provide a nondestructive acoustic inspection system which is capable of measuring the thickness of each layer in a laminated or multilayer article.

Another object of the present invention is to provide an ultrasonic inspection system which is capable of detecting the thickness of layers at least as thin as one mil with a high degree of accuracy, e.g., approximately 0.2 mils.

Still another object of the present invention is to provide a reliable ultrasonic testing apparatus which receives at least one echo signal from each layer interface in a multilayer article.

Yet another object of the present invention is to provide a nondestructive inspection apparatus for inspecting non-rigid multilayer or laminated articles.

A further object of the present invention is to provide a nondestructive inspection system for detecting interfaces as little as one mil apart.

Other objects and advantages of the present invention will be set forth in part in the description and drawings which follow, and, in part, will be obvious from the description, or may be learned by practice of the invention.

As embodied and broadly described herein, an apparatus for inspecting a multilayer object according to the present invention comprises means for positioning the object in an inspection position, means for transmitting at least one focused acoustic pulse into the object from opposite sides thereof, means for receiving reflections of portions of the acoustic pulses from layer interfaces within the object and converting the received acoustic reflections into electrical signals, and means for analyzing the electrical signals to determine the thickness of layers in the object. Preferably, the positioning means includes a clamping device for precisely positioning the object relative to the transmitting means so that the acoustic pulses are focused at predetermined positions within the object. For example, in one embodiment of the invention, the focused acoustic pulses may be focused at a substantially common point within the object. The acoustic pulses are preferably generated sequentially.

The positioning means may also include a device for holding the object during an inspection sequence. The apparatus may further comprise a tank for holding a liquid and a liquid acoustic transmission medium in the tank, wherein the holding device holds the object in the acoustic transmission medium. Additionally, the apparatus may comprise means for selectively positioning at least portions of the transmitting means, receiving means and clamping means in the acoustic transmission medium for inspection of the object.

In order to facilitate the detection and resolution of manufacturing or test problems, the apparatus may further comprise means for marking the object proximate to each inspection position. The apparatus may also comprise means for sensing whether the object is positioned within predetermined positioning parameters for inspection. Preferably, the apparatus additionally comprises means for moving at least some portion of the clamping means, the transmitting means and the receiving means to permit inspection of the object at different inspection positions. The transmitting means also preferably comprises first and second focused ultrasonic transducers and the apparatus preferably further comprises means for storing data pertaining to the thickness of each layer in the object. The first and second focused transducers are mounted so that acoustic pulses generated therefrom pass at least in part through openings in first and second clamp sleeves of the clamping means, the first and second clamp sleeves clamping the object from opposing sides thereof.

A method for determining the thickness of each layer in a multilayer object according to the present invention comprises the steps of transmitting at least one focused acoustic pulse into the object from opposing sides thereof at a first cross section of the object, receiving reflections of the transmitted acoustic pulses from interfaces, including outer surfaces and internal interfaces, and converting the received reflections into electrical signals, analyzing the electrical signals to determine the thickness of each layer at the cross section, and repeating the transmitting, receiving and analyzing steps for subsequent cross sections to be inspected. Preferably, a computer controls the inspection of the object, and the method further comprises the step of inputting data to the computer regarding an inspection to be carried out and data regarding the object to be inspected to the computer. The input data may include predetermined tolerances for the thickness of each layer, wherein an operator is alerted and the inspection procedure can be halted when one or more of the determined layer thicknesses does not fall with its corresponding tolerances. The method may also comprise the step of automatically sensing whether the object is positioned within predetermined position parameters for inspection and the step of marking the object proximate to each inspected cross section. Additionally, the acoustic pulses are preferably transmitted sequentially in the transmitting step, and the acoustic pulses preferably comprise focused ultrasonic pulses. Preferably, the method also includes the step of clamping the object proximate to the cross section to be inspected to insure that the pulses have focal points at substantially predetermined positions within the object.

The present invention will now be described with reference to the following drawings, in which like reference numbers denote the same elements throughout.

BRIEF DESCRIPTION OF THE DRAWINGS

FIG. 6 a front view of the nondestructive inspection system of FIG. 1.

DESCRIPTION OF AN PREFERRED EMBODIMENT

An embodiment of the present invention will now be described with reference to the inspection of multilayer plastic. Plastic produced in laminate forms is widely used to form plastic products, such as food containers. Multilayer plastic is typically produced in what is known as web form. These webs generally have a width of several feet and a length in the dozens or hundreds of feet. When inspecting such sheets for quality, it is preferred that the thickness of each layer in the plastic sheet be measured at points across the width of the web to ensure the quality of the web. Typically, test results are collected and catalogued and function to guarantee that the plastic sheet will perform the function demanded of it.

Figure 1:
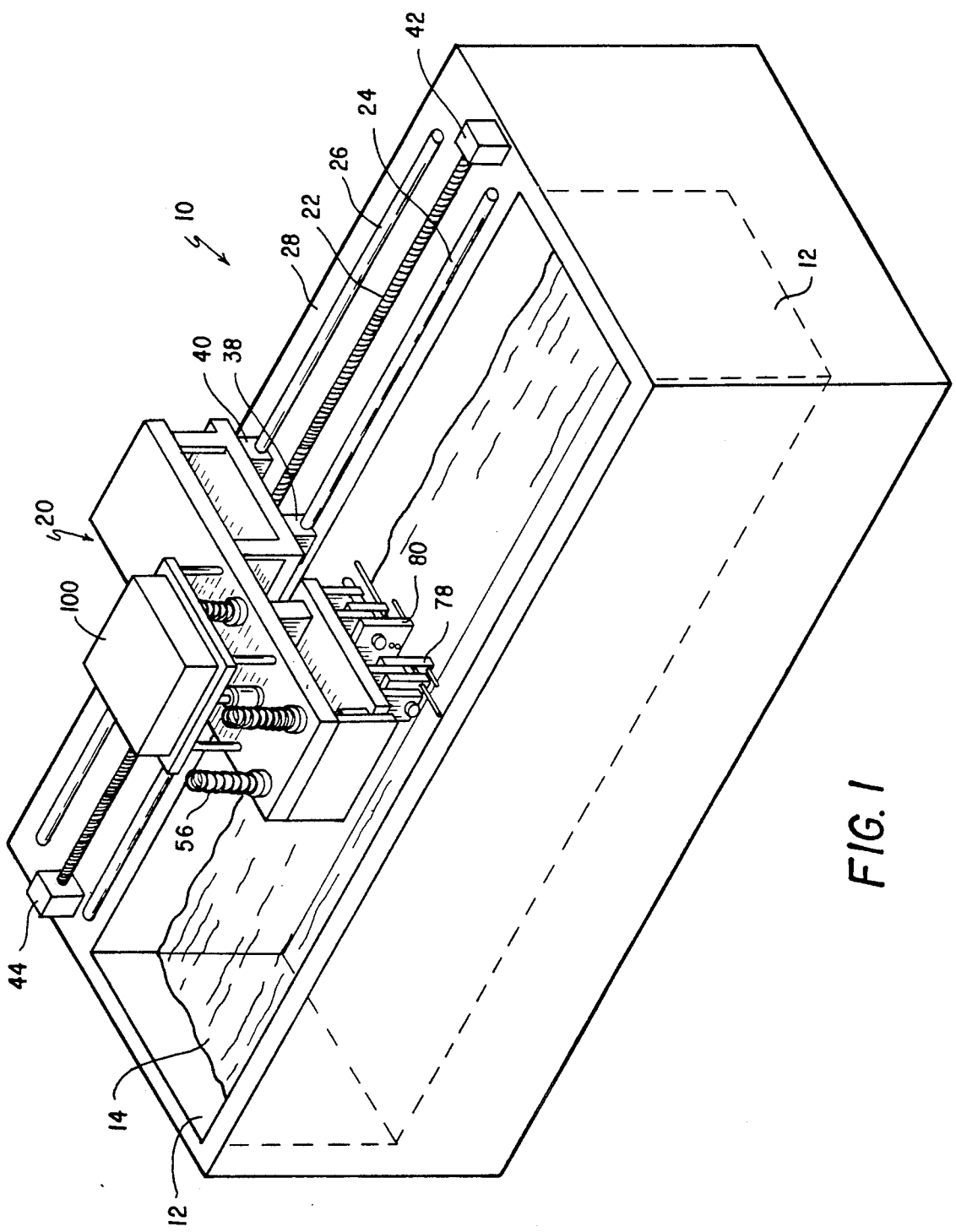
FIG. 1 is a perspective view of an embodiment of a nondestructive inspection system according to the present invention.

Referring now to FIG. 1, an inspection unit 10 having a tank 12 is provided. The tank 12 is preferably at least six feet long, to accommodate a strip from the width of a typical plastic sheet, and is designed to contain a liquid 14 suitable for use with acoustic testing. An appropriate liquid, such as water, provides an appropriate interfacing medium between the face of acoustic generating means and the surface of an article being inspected. Preferably, the inspection unit 10 is connected directly to a domestic water source and includes a reverse osmosis system (not shown) which treats water to be held in the tank 12. Although distilled water and other liquids can be employed as the interfacing medium, the inclusion of a reverse osmosis system permits a permanent connection to a domestic water source. This should ensure that the tank 12 will always remain full and thus that the inspection unit 10 will not be subject to down time from water loss due to water evaporation and the like or from the nonavailability the appropriate liquid. Preferably, the tank 12 further includes a filtration system (not shown) for keeping the interfacing medium 14 free of particles or other debris that could effect the acoustic energy to be transmitted therethrough.

Figure 2A:
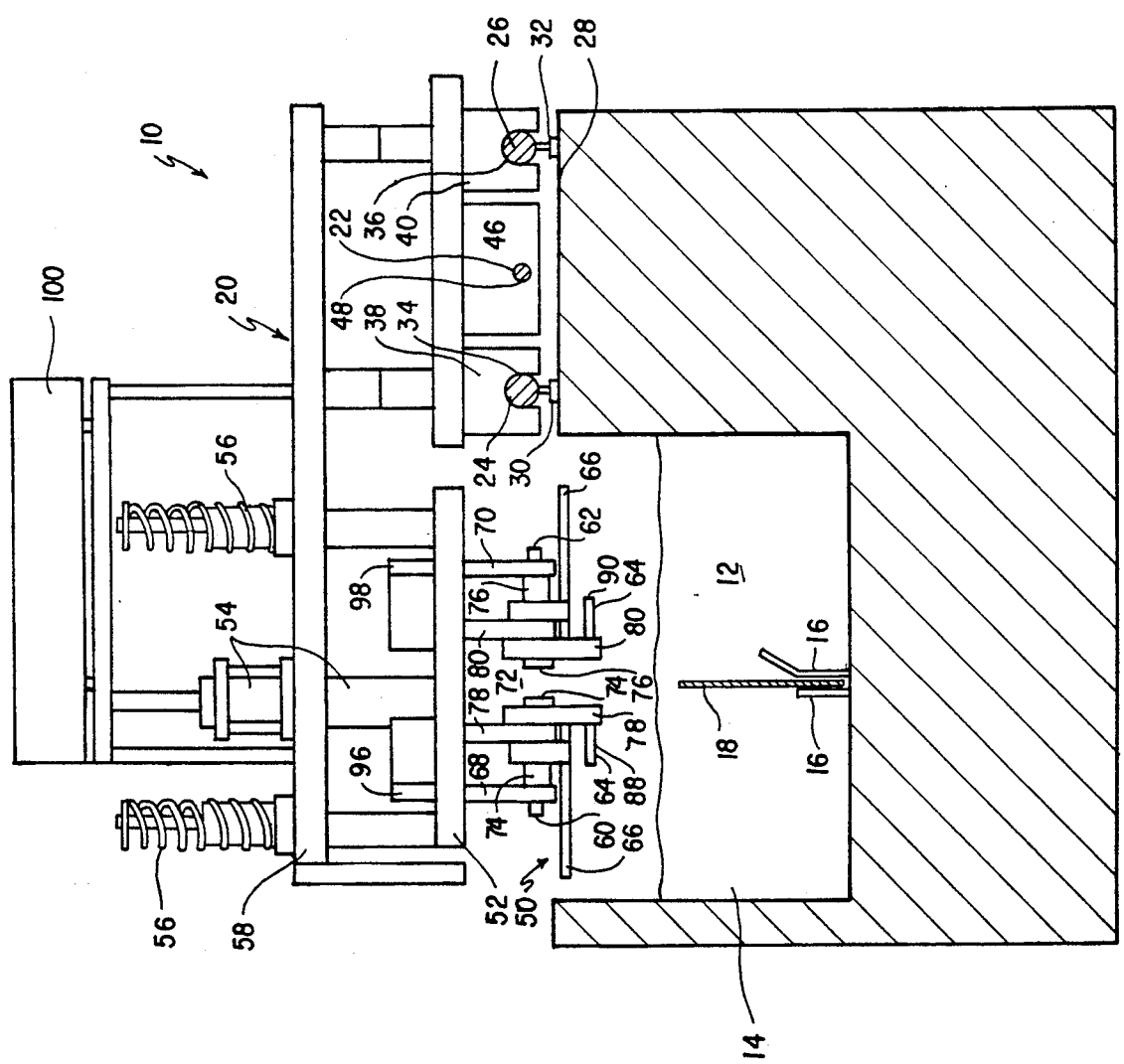
FIG. 2A is a side view, partially in cross section, of the nondestructive inspection system of FIG. 1.

As best illustrated in FIG. 2A, the inspection unit 10 also includes a holding device 16 located along the length of and substantially centered on the bottom surface of the tank 12. The holding device 16 is preferably pneumatically driven, and functions to hold an article 18 to be inspected, such as a strip of multilayer plastic from a plastic sheet, in position for subsequent inspection. Of course, the holding mechanism and the tank dimensions can be modified to accommodate the article or articles to be inspected. Further, and as will be discussed below, the holding device 16 is supplemented by a clamping means to ensure precision positioning of articles, and particularly non-rigid articles, such as plastic sheets, relative to the acoustic generating means.

A carrier 20 is movably mounted on the unit 10 relative to the tank 12 such that the carrier 20 can traverse the length of the tank and thus the entire article 18. Movement along the length of the tank 12 is provided by an arrangement which includes a rotatable lead screw 22 which is mounted parallel to and between a pair of cylindrical rods 24, 26. As best illustrated in FIGS. 1 and 2A, the rods 24, 26 are supported substantially parallel to and above a surface 28 of the unit 10 by respective mounts 30, 32. The carrier 20 rides along and is supported by the rods 24, 26 via grooves 34, 36 in guides 38, 40, respectively, which are fixedly mounted to the carrier 20 and formed to surround most of the rods 24, 26. Ball bearings or the like (not shown) are mounted in the guides 38, 40 so that they extend through the surfaces of the grooves 34, 36 and provide means for permitting the guides 38, 40 to freely move along the rods 24, 26.

Motion of the carrier 20 along the rods 24, 26 is provided by rotation of the lead screw 22. The lead screw 22 is mounted on the surface 28 at one end by a mount 42, which permits the lead screw 22 to freely rotate therein, and at the other end by a motor 44 which rotates the lead screw 22. The motor 44 can be controlled by a computer, as will be explained below. A threaded guide 46 mounted on the carrier 20 between the rod guides 38, 40 includes a threaded internal opening 48 therethrough in which the lead screw 22 is threaded. By rotating of the lead screw 22, the lead screw moves relative to the threaded guide 46 propelling the carrier 20 along the rods 24, 26.

The carrier 20 is cantilevered over the tank 12 so that a portion thereof permanently extends over the tank 12. Inspection equipment 50 extends from the bottom surface of an inspection equipment mounting plate 52 of the carrier 20 over the tank 12. The mounting plate 52 is movable in the vertical direction down by a pneumatically driven piston 54 so that the equipment 50 can be placed into the liquid 14 about the article 18, which is held by the holding device 16 to permit the equipment 50 to be lowered without interference from the article 18. A set of four springs 56 mounted on an upper portion 58 of the carrier 20 are attached to the mounting plate 52 to provide an upward vertical force to remove the equipment 50 from the liquid 14 when electrical power and/or pneumatic pressure are turned off. This ability keeps the equipment 50 out of the liquid 14 when the equipment 50 is not in use and increases the life of the equipment 50.

Figure 2B:
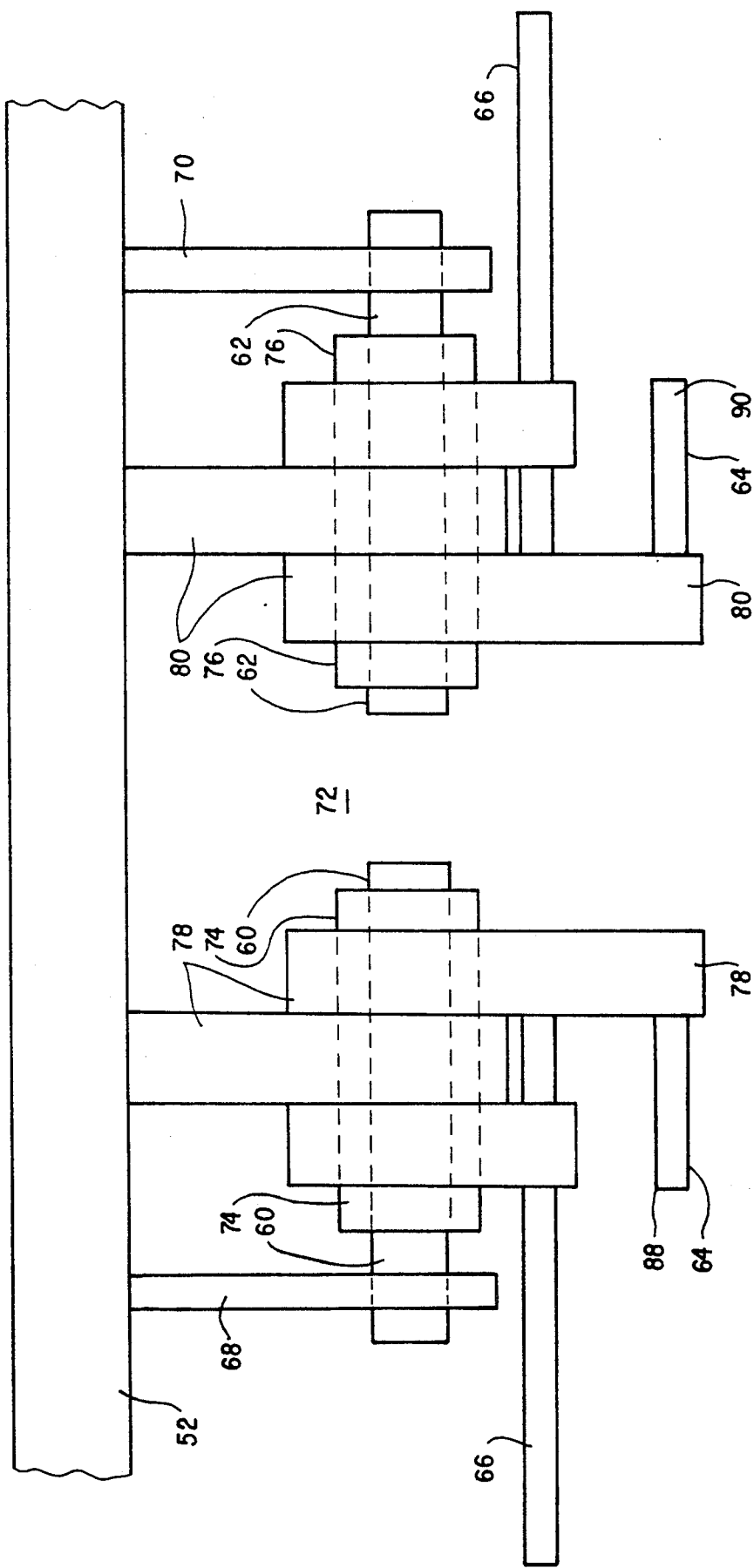
FIG. 2B is a detailed side view of a portion the inspection equipment of the system of FIG. 1 showing the clamping means, transmission means and receiving means.

As best illustrated in FIG. 2B, the equipment 50 includes two transducers 60, 62 for producing the acoustic energy, an optical sensor 64 and an inspection position marker 66. The transducers 60, 62 are preferably focused ultrasonic transducers which output signals of at least 50 MHz. The transducers 60, 62 are attached to the mounting plate 52 via mounts 68, 70, respectively, so that the transducers 60, 62 are coaxial and in a facing relationship so as to measure the same cross section of the article 18 from opposite sides thereof.

Figure 5:
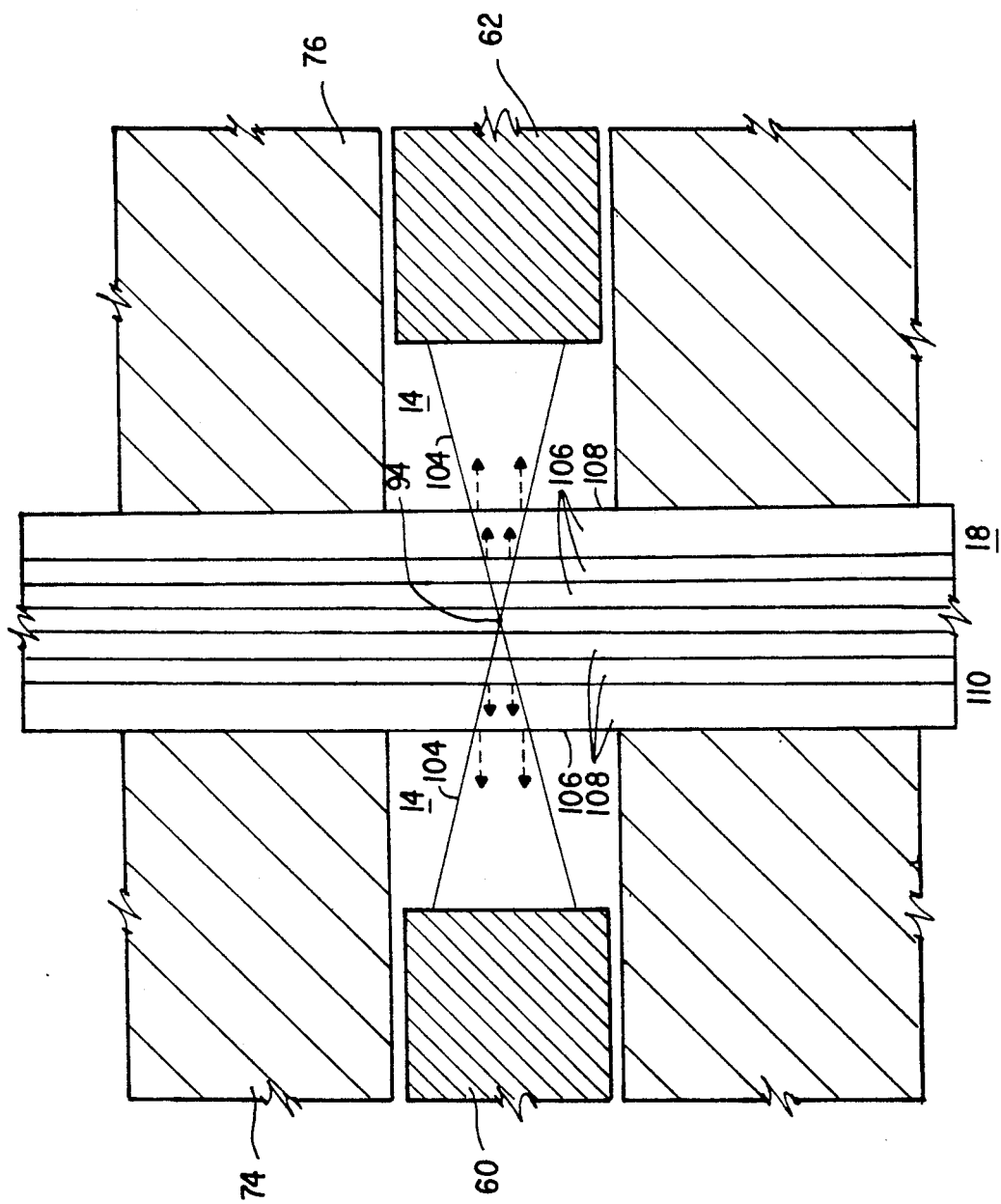
FIG. 5 schematically illustrates inspection of a multilayer article using the nondestructive inspection system of FIG. 1.

A clamp 72 is also included to provide a clamping function which ensures proper positioning of the article 18 relative to the transducers 60, 62 so that the focal points of the acoustic signals transmitted by the transducers 60, 62 will be located at predetermined positions during inspection of the article 18. The clamp 72 comprises two facing clamp sleeves 74, 76 which are also pneumatically actuated and are attached to the mounting plate 52 via mounts 78, 80, respectively. Each of the clamp sleeves 74, 76 includes an opening therethrough for the transducers 60, 62. The clamp sleeves 74, 76 and the transducers 60, 62 are not connected and move independently. Typically, each transducer will extend through the opening in its associated clamp sleeve when the clamp 72 is open, but will not extend therethrough when the clamp 72 is closed, as is illustrated in FIG. 5. The optical sensor 64 and the marker 66 are mounted in the mounts 78, 80 and will be discussed in more detail below.

Figure 3A:
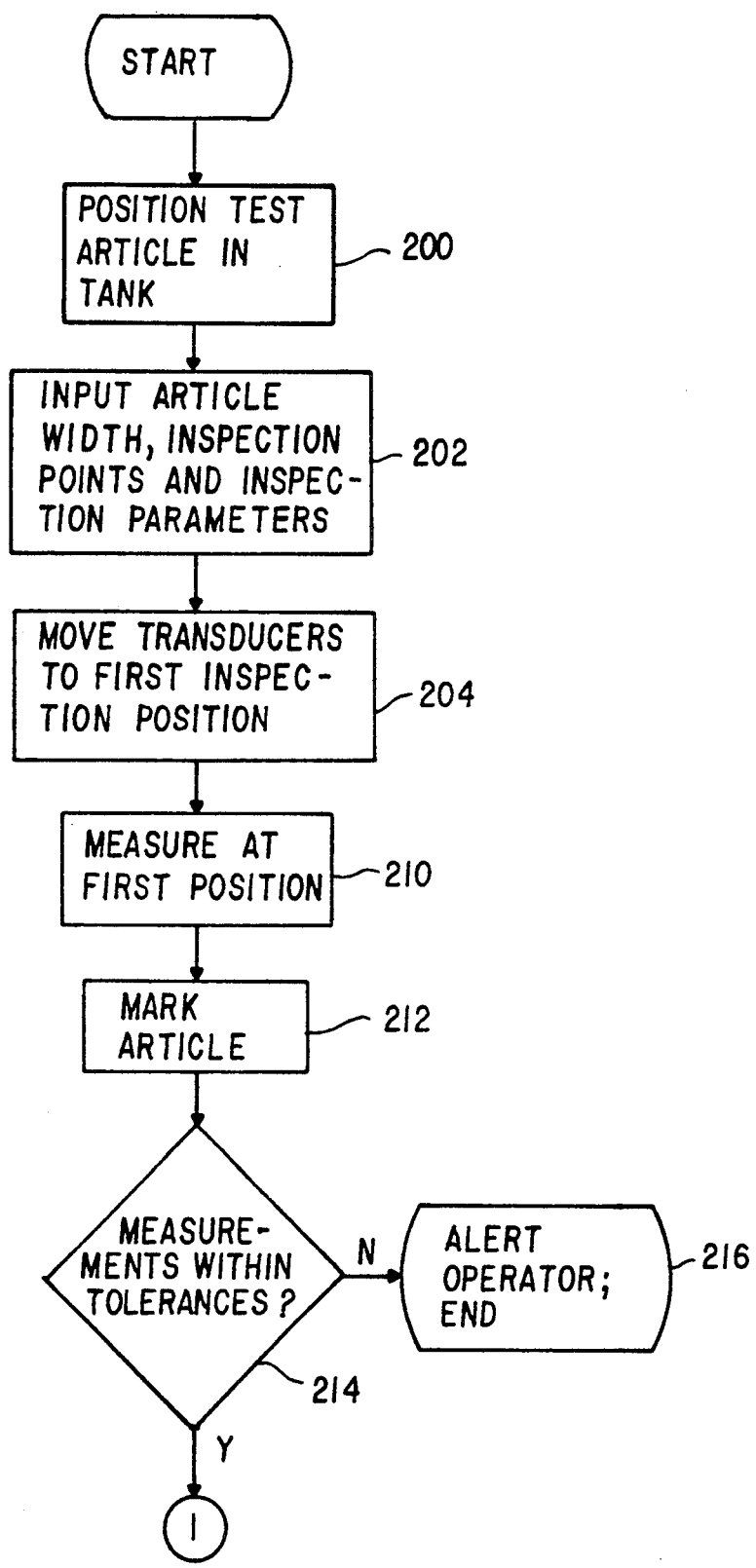
FIGS. 3A-3B are a flowchart of an inspection process using the inspection system according to the present invention.
Figure 3B:
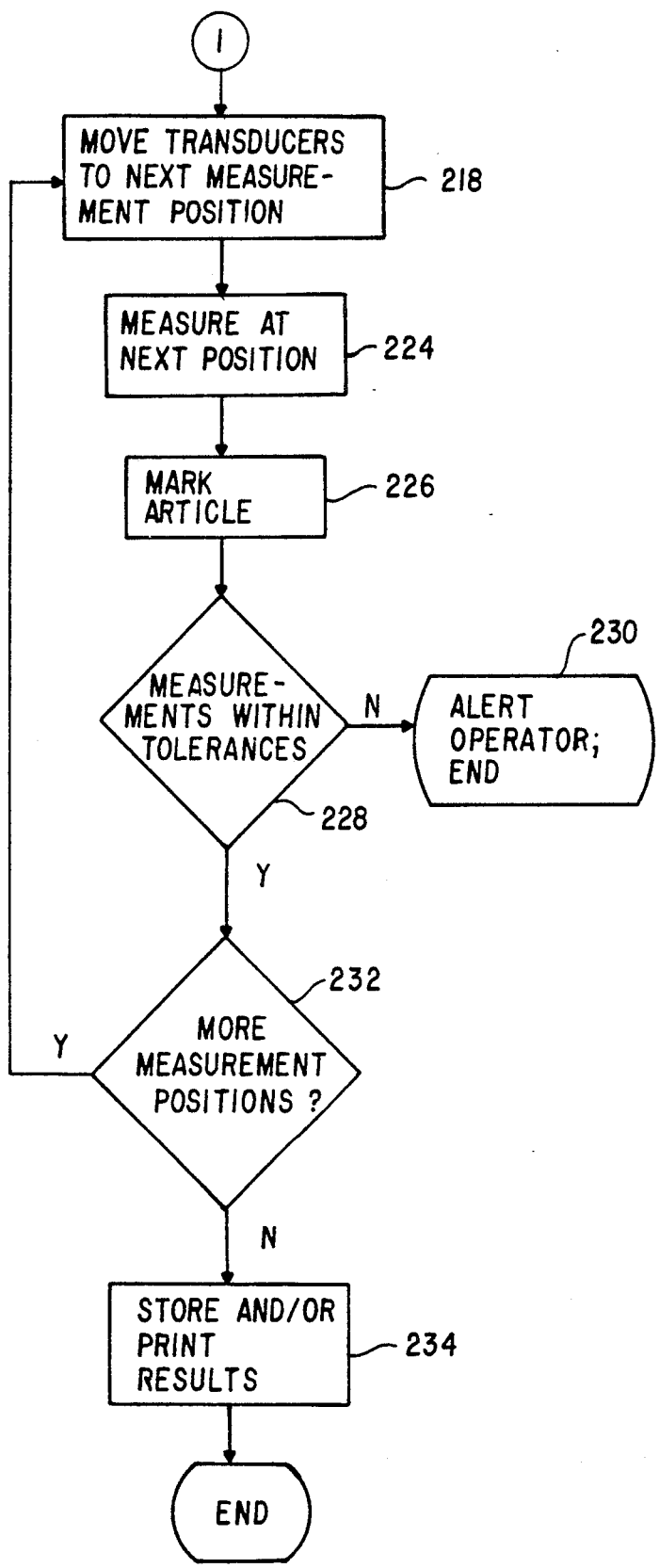
Figure 4:
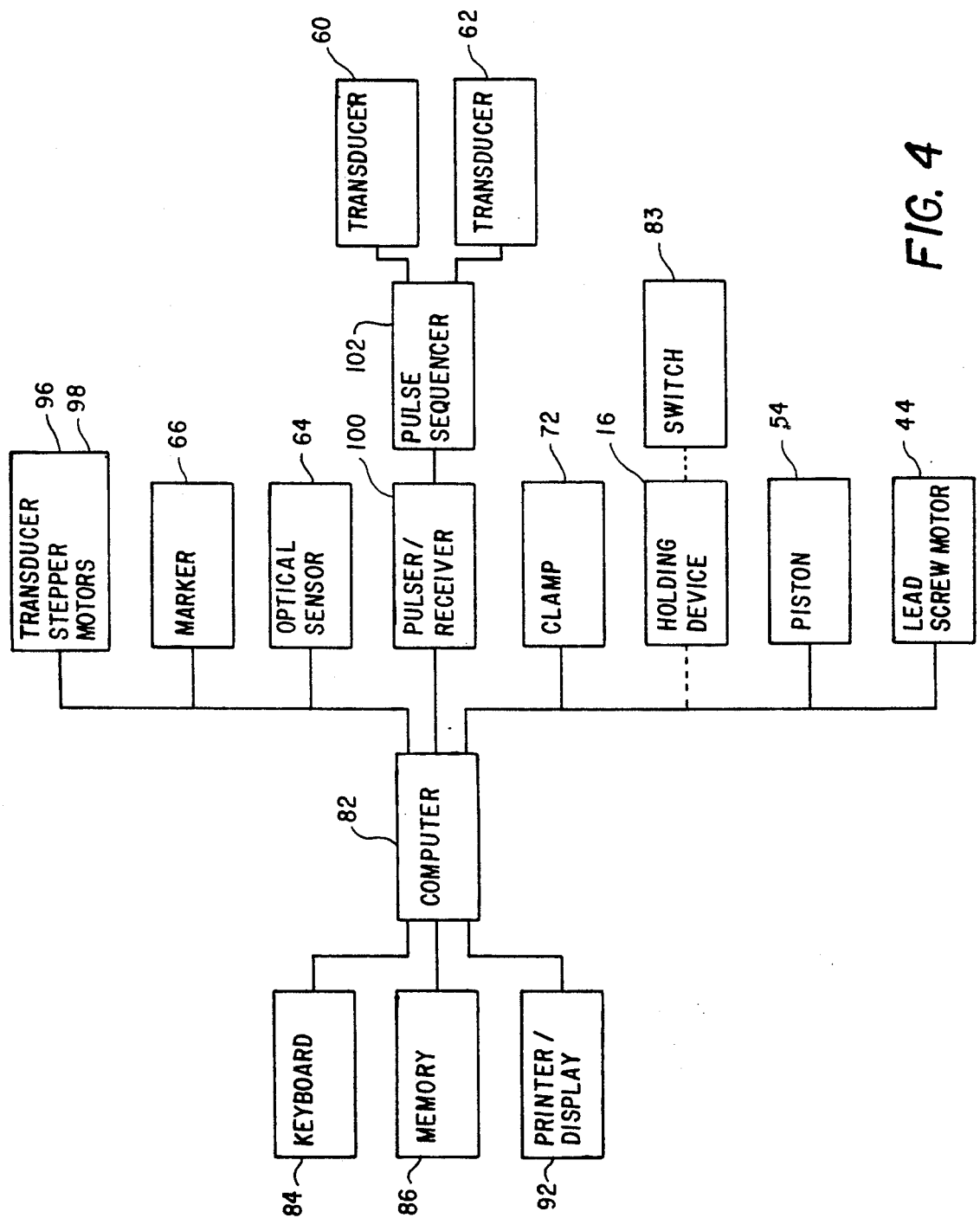
FIG. 4 is a block diagram of the electronic interfaces of the system of FIG. 1.

The operation of the inspection system will now be described with reference to the flowchart of FIGS. 3A-3B, the electronic schematic of FIG. 4, and the views provided in FIGS. 5 and 6. Control of the inspection unit 10 is provided by a computer 82. In accordance with known techniques, the computer 82 provides commands to provide the desired movements of the carrier 20 and piston 54. The computer 82 also controls the optical sensor 64 and receives and processes information therefrom and controls the marker 66, as is discussed below. An article 18 to be inspected, such as a plastic sheet, is positioned in the open holding device 16 (step 200). A manual switch 83 is then operated to close the holding device 16 about the article 18. Data is input into the computer 82 (FIG. 4) regarding the inspection to be performed. The anticipated thickness of the sheet 18 should be input, and other data, for example, the length of the sheet 18, the number of layers anticipated to be found within the sheet 18, the sound velocity of ultrasonic energy through each layer, the number of measurements to be taken of the sheet 18, the distance between measurement (inspection) points, the anticipated results, and acceptable tolerances, may be input to the computer 82 (step 202). This data can be input directly for each article to be inspected via a keyboard 84, but the data is preferably stored in memory 86 and is accessible by a simple command, since the same inspection sequence will typically be performed on each of a series of the same article.

The inspection sequence is started by an input command or manipulation of a switch. The computer 82 causes the motor 44 to rotate the lead screw 22 and thereby move the carrier 20 to a first position along the length of the sheet 18. Preferably, when the inspection equipment 50 is in an "up" position, the components which comprise the optical sensor 64 will be above the top of the sheet 18. The optical sensor 64 can then be used to ensure that the sheet 18 has not been mispositioned in the holding device 16 so that it extends too high and/or that the sheet 18 is not too large and will not damage the inspection equipment 50 when it is lowered. An optical transmitter 88 and an optical receiver 90 comprise the optical sensor 64 and are mounted in respective mounts 78, 80 so that they extend through the mounts 78, 80 in a facing relationship and in vertical alignment with respective transducers 60, 62. Under control of the computer 82, radiation of an appropriate wave length is transmitted from the optical transmitter 88. If the radiation is not received by the optical receiver 90, then it is presumed that the sheet 18 is not in position or is too large. In this case, the computer 82 alerts the operator via, for example, a printer or other display device 92 or some type of alarm, and ends the inspection sequence.

If the optical receiver 90 receives the radiation, the inspection sequence is continued. The computer 82 then controls the piston 54 to lower the inspection equipment 50 into the liquid 14 so that the transducers 60, 62 are both substantially normal to and on opposite sides of the plastic sheet 18 at a first inspection position (cross section) of the sheet 18 (step 204). Based on the input data, the transducers 60, 62 are positioned so that their respective focal points are substantially at desired predetermined points within the plastic sheet 18. Preferably, in the embodiment shown, the focal points are at a substantially common point 94 in the interior of the plastic sheet 18. In cases in which the plastic is relatively symmetrical in terms of layers and layer characteristics, the common focal point will preferably be nominally at the center of plastic sheet 18 after the clamp sleeves 74, 76 are closed. Positioning of the focal points of the transducers 60, 62 is controlled by the computer 82 via corresponding stepper motors 96, 98 (FIG. 2A), which move the transducers 60, 62 along their common axis using known techniques. The relative positions of the transducers 60, 62 with respect to the cross section of the sheet 18 will remain fixed for the entire inspection sequence. Given that the distance from the face of each transducer to its focal point should be known and that the transducers 60, 62 are mounted so that they are substantially coaxial, appropriate manipulation of the stepper motors 96, 98 should provide the substantially common focal point 94.

After the transducers 60, 62 are positioned, the computer 82 causes the clamp sleeves 74, 76 to close on the sheet 18 to provide final clamping of the sheet 18 and ensure proper positioning of the sheet 18 relative to the transducers 60, 62. For example, the closing of the pneumatically-actuated clamp sleeves 74, 76 on the plastic sheet 18 from either side thereof centers the sheet 18 between the transducers 60, 62, ensures that the surfaces of the plastic sheet 18 are substantially normal to the transducers 60, 62 and aids in positioning the sheet 18 so that the common focal point 94 is proximate to the desired location in the sheet 18. The movement of the clamp sleeves 74, 76 is pneumatically actuated and under the control of the computer 82. For example, during a clamping procedure, the sleeve 74 is first moved toward the sleeve 76 until it reaches a mechanical stop in the actuator. The sleeve 76 is then moved toward the sleeve 74 until it closes on the plastic sheet 18 and holds it against the clamp sleeve 74.

In the preferred embodiment, an ultrasonic pulser/receiver 100 is mounted on the carrier 20. The pulser/receiver 100 is operated under control of the computer 82. In response to a signal from the computer 82, the pulser/receiver 100 preferably generates and sends one electrical pulse to each of the transducers 60, 62 via a pulse sequencer 102 (FIG. 6). This causes a focused ultrasonic pulse 104 to be transmitted first by one transducer and then the other. The focused pulse 104 from each transducer passes through the liquid 14 in the tank 12 and enters the plastic sheet 18. As shown in part in FIG. 5, a portion of each pulse 104 is reflected from the surfaces 106 and each interface 108 between layers 110 in the sheet 18 back to the transmitting transducer, where the received reflections are converted to electrical signals and sent to the computer 82 via the pulser/receiver 100. The electrical signals can then be analyzed in accordance with known techniques to provide layer thicknesses from the perspective of each transducer as far into the sheet 18 as each pulse is able to penetrate and provide a sufficient reflection.

In conventional inspection systems, attenuation of the ultrasonic pulse is a major problem in the inspection of multilayer articles, and inaccuracy is a problem when very thin layers are present. The inventors have found that by using a focused pulse, thicker multilayer sheets can be inspected before attenuation becomes a problem. Also, superior results are provided when layer thicknesses are as little as one mil or even less. However, even with a focused pulse, depending on the composition of the material and thickness of the material, results can deteriorate due to attenuation after traveling through, for example, 60 to 70 mils of material and/or a number of layer interfaces. Additionally, reliability becomes suspect when the inner layers are very thin. In this regard, the inventors have found that a second focused pulse which enters the article from the opposite side provides accurate measurement of the outer layers closest to the opposite side, layers which would not be accurately measured by the first pulse. Additionally, the second pulse provides a second measurement of the interior layers, such as a central barrier layer, which can improve the statistical accuracy of the measurement. This second measurement can be critical when these layers are sub-mil in thickness. As discussed above, by the time the ultrasonic pulses reach the interfaces associated with these layers, the pulses have lost much of their intensity. However, since the thickness of these layers is measured twice, reliability and accuracy of the measurement are increased. In the present invention, the computer 82 first calculates each thickness in accordance with standard techniques, and then calculates the mean of the two measurements for the interior layers, which is output as the calculated thickness for these layers. Further, since the total number of layers should be known, the results from the two transducers are combined so that the output or stored data includes a single measurement of the thickness of each layer.

Following the measurement at the first inspection point on the plastic sheet 18, the plastic sheet 18 is marked on at least one side by the computer-controlled pneumatically actuated marker 66 proximate to the inspection point (step 212). Preferably, the marker 66 leaves an indentation in one side of the plastic sheet 18 in a vertical relationship to the actual inspection point and a known distance therefrom. When results are made available to the operator, if a problem with a certain inspection position is discovered, that inspection position can be readily identified on the sheet 18. If an error is indicated, this will assist in trouble shooting of the manufacturing device, as the precise position of the defect relative to the production machinery can readily be determined. The marking also permits the use of other techniques to study the layer structures at the appropriate point to better understand sheet structure problems.

The calculated thickness of the layers of the plastic sheet 18 can then be checked against expected values (step 214). If one or more layer thicknesses do not fall within predetermined tolerances, the operator is alerted of the situation (step 216) and/or the measurement procedure is automatically stopped. Typically, the operator would verify that the inspection sequence being carried out is appropriate for the article being inspected, and/or that the proper data has been input to the computer 82. If either is improper for the article 18 being inspected, the appropriate sequence can be selected and/or data loaded and the inspection sequence restarted. If these are not the problem, then recalibration of the inspection equipment 50 may be necessary, or a manufacturing error may be occurring.

If the measurements are within the tolerances, the clamp sleeves 74, 76 are opened, and the appropriate steps taken to move the transducers 60, 62 relative to the article 18 to the next inspection position for the article 18 (step 218). This can involve simply vertical movement of the equipment 50, or movement of the carrier 20 with respect to the article 18, or a combination of both. If the equipment 50 is raised to a pre-test height prior to being lowered to the subsequent measurement position, the optical sensor 64 may be employed to verify that the sheet 18 is correctly positioned and not too large, as discussed relative to the first inspection position. In any case, upon arrival at the next measurement position, the clamp sleeves 74, 76 are closed, and an ultrasonic pulse is introduced sequentially from each transducer 60, 62 to the article 18 from either side of the article 18. The computer 82 then calculates the thickness of each layer (step 224), as discussed relative to step 210. The inspection position is then marked by the marker 66 (step 226), and the measurements compared to expected measurements for conformance to predetermined tolerances (step 228). As before, if the measurements not within tolerance, the operator is alerted and the inspection sequence ended (step 230).

The computer 82 then determines whether there are more inspection points for inspection (step 232). If more measurement points exist, then steps 218 through 232 are repeated for the subsequent positions. When there are no more positions to be measured, the computer 82 stores the determined layer thicknesses for each layer at each inspection point in the memory and/or prints or otherwise displays the results on the output device 92 (step 234). Alternatively, results can be displayed, printed and/or stored as soon as they are available during the inspection sequence. The system is then ready for the next article to be inspected.

While one embodiment of the present invention has been discussed, it will be appreciated by those skilled in the art that various modifications and variations are possible without departing from the spirit and skill of the invention.

What is claimed is:

1. An apparatus for inspecting a multilayer object, comprising:
   means for positioning the object in an inspection position;
   means for transmitting at least one focused acoustic pulse into the object from each of two opposing sides of the object;
   said positioning means including means for clamping the object proximate to a cross-section of the object to be inspected to ensure that the focused acoustic pulses are focused at respective predetermined positions within the object;
   means for receiving reflections of portions of the acoustic pulses from layer interfaces within the object and converting the received reflections into electrical signals; and
   means for analyzing the electrical signals to determine the thickness of layers in the object.

2. An apparatus for inspecting a multilayer object, comprising:
   means for positioning the object in an inspection position;
   means for transmitting at least one focused acoustic pulse into the object from each of two opposing sides of the object;
   clamping means for ensuring positioning of the object relative to said transmitting means so that the focused acoustic pulses are focused at a substantially common point within the object;
   means for receiving reflections of portions of the acoustic pulses from layer interfaces within the object and converting the received reflections into electrical signals; and
   means for analyzing the electrical signals to determine the thickness of layers in the object.

3. An apparatus for inspecting a multilayer object according to claim 1, wherein the focused acoustic pulses are generated sequentially.

4. An apparatus for inspecting a multilayer object according to claim 1, wherein said positioning means further includes means for holding the object during an entire inspection sequence.

5. An apparatus for inspecting a multilayer object according to claim 4, further comprising:
   a tank;
   a liquid acoustic transmission medium in said tank wherein the multilayer object is held by said holding means in said acoustic transmission medium; and means for selectively placing at least a portion of said transmitting means, said receiving means and said holding means in said acoustic transmission medium.

6. An apparatus for inspecting a multilayer object according to claim 1, further comprising means for marking the object at a position proximate to where the acoustic pulses enter the object.

7. An apparatus for inspecting a multilayer object according to claim 1, further comprising means for storing data pertaining to the thickness of each layer in the object.

8. An apparatus for inspecting a multilayer object according to claim 1, further comprising means for moving at least some portion of said clamping means, said transmitting means, and said receiving means to permit inspection of different positions of the object.

9. An apparatus for inspecting a multilayer object, comprising:

means for positioning the object in an inspection position, comprising first and second clamp sleeves for clamping the object from two opposing sides, the first and second clamp sleeves including respective openings therethrough for passage of acoustic pulses;

means for transmitting at least one focused acoustic pulse into the object from each of the two opposing sides of the object, said means for transmitting comprising first and second focused ultrasonic transducers;

means for receiving reflections of portions of the acoustic pulses from layer interfaces within the object and converting the received reflections into electrical signals; and means for analyzing the electrical signals to determine the thickness of layers in the object.

10. An apparatus for inspecting a multilayer object according to claim 1, wherein said clamping means clamps the object relative to said transmitting means wherein the focused acoustic pulses to be transmitted are substantially normal to said two opposing sides of the object.

11. An apparatus for inspecting a multilayer object according to claim 1, further comprising means for sensing whether the object is positioned within position parameters for inspection.

12. A method for determining the thickness of each layer in a multilayer object for at least one cross section in the multilayer object for at least one cross section in the object, comprising the steps of:

(a) clamping the object proximate to a cross section to be inspected;

(b) transmitting at least one focused acoustic pulse into the object from each of two opposing sides of the object at the cross section, the focused acoustic pulses have focal points at substantially predetermined positions within the object;

(c) receiving reflections of the transmitted acoustic pulse form interfaces and converting the received reflections into electrical signals;

(d) analyzing the electrical signals to determine the thickness of each layer at the cross section; and (e) repeating said steps (a) through (d) for subsequent cross sections to be inspected.

13. A method according to claim 12, further comprising, prior to said step (a), the step of (f) inputting data regarding an inspection to be carried out and data regarding the object to be inspected to a computer, and wherein the computer controls the inspection of the object.

14. A method according to claim 13, wherein said step (f) further comprises inputting predetermined tolerances for each layer to the computer, and said step (d) further comprises alerting an operator when at least one of the determined thicknesses does not fall within its corresponding predetermined tolerance.

15. A method according to claim 12, further comprising, prior to said step (a), the step of (g) automatically sensing whether the object is positioned within position parameters for inspection.

16. A method according to claim 12, further comprising, following said step (c), the step of (h) marking the object proximate to the inspected cross section.

17. A method according to claim 12, wherein said step (b) further comprises sequentially transmitting the focused acoustic pulses.

18. A method according to claim 12, wherein the focused acoustic pulses are focused ultrasonic pulses.

* * * * *